United States Patent [19]

Olsen

[11] Patent Number: 5,393,658
[45] Date of Patent: Feb. 28, 1995

[54] IMMUNOASSAY METHOD FOR THE RAPID IDENTIFICATION OF DETERGENT TREATED ANTIGENS

[75] Inventor: Duane A. Olsen, Tacoma, Wash.

[73] Assignee: New Horizons Diagnostics Corporation, Columbia, Md.

[21] Appl. No.: 42,749

[22] Filed: Apr. 6, 1993

Related U.S. Application Data

[63] Continuation of Ser. No. 742,734, Aug. 6, 1991, abandoned, which is a continuation of Ser. No. 101,417, Sep. 28, 1987, abandoned.

[51] Int. Cl.$^6$ ............... G01N 33/751; G01N 33/53; G01N 33/553
[52] U.S. Cl. .................. 435/7.36; 435/7.1; 435/7.32; 435/7.2; 435/961; 435/975; 436/518; 436/525; 436/536; 436/538; 436/174
[58] Field of Search ............ 435/7.32, 7.36, 7.33, 435/7.34, 7.35, 7.37, 961, 971, 29, 7.1, 7.2, 975; 436/518, 525, 528, 527, 536, 538, 174; 422/101

[56] References Cited

U.S. PATENT DOCUMENTS

| | | | |
|---|---|---|---|
| 4,313,734 | 2/1982 | Leuvering | 436/518 |
| 4,459,361 | 7/1984 | Gefter | 436/532 |
| 4,497,900 | 2/1985 | Abram et al. | 435/7.36 |
| 4,552,839 | 11/1985 | Gould et al. | 436/824 |
| 4,623,461 | 11/1986 | Hossom et al. | 210/445 |
| 4,707,543 | 11/1987 | Zollinger et al. | 530/402 |
| 4,847,199 | 7/1989 | Snyder et al. | 435/36 |
| 4,948,726 | 8/1990 | Langoria | 435/7.92 |

OTHER PUBLICATIONS

Corbel et al, J. Hyg. Camb., vol. 68, 1970, pp. 81–96.
Mukhlis et al, Vaccine, vol. 4, Sep. 1986, pp. 192–196.
Caldwell et al, Infection and Immunity, vol. 31(3), Mar. 1981, pp. 1161–1176.
Sato et al., JNCI, vol. 74(4), Apr. 1985, pp. 883–888.
Teerlink et al, Biological Abstracts, Abstract No. 37643, 1987.
Bessen et al, Biological Abstracts, Abstract No. 66204, 1987.
Zierdt et al. "Adherence of Bacteria, Yeast, Blood Cells, and Latex Spheres to Large–Porosity Membrane Filters", *App. and Environ. Micro.*, 38(6): 1166–1172 (1979).

Primary Examiner—Carol E. Bidwell
Attorney, Agent, or Firm—Foley & Lardner

[57] ABSTRACT

An assay is provided in which a target ligand is detected in a biological specimen. The method involves treating the target ligand with detergent and then binding the treated ligand to a particle by means of a capturing substance on the particle, thereby forming a complex. The complex is then applied to a porous membrane having a charge similar to that of a glass fiber filter in order to immobilize the complex in the porous membrane. The pore size of the membrane is substantially larger than the size of the complex such that the immobilization of the complex is substantially accomplished by means of the attraction of the complex to the charge of the porous membrane, and not as a function of the pore size of the membrane. Thereafter, the presence of the complex in the porous membrane is detected.

19 Claims, No Drawings

IMMUNOASSAY METHOD FOR THE RAPID IDENTIFICATION OF DETERGENT TREATED ANTIGENS

This application is a continuation of application Ser. No. 07/742,734, filed Aug. 6, 1991 now abandoned, which is a continuation of Ser. No. 07/101,417, filed Sep. 28, 1987 (abandoned).

FIELD OF INVENTION

The present invention relates to an immunoassay wherein the immune complex formed between a colloidal gold labeled antibody and respective detergent treated antigen becomes immobilized on the surface of certain porous materials.

BACKGROUND OF THE INVENTION

The isolation, rapid identification and confirmation of *Neisseria gonorrhoeae* is of extreme importance in the diagnosis and treatment of the symptomatic and asymptomatic cases which are part of the worldwide gonorrhea epidemic. In addition early detection of disease is of utmost importance since undetected gonorrhea infections can lead to serious complications such as pelvic inflammatory disease, sterility, arthritis and blindness.

Infection with *Neisseria gonorrhoeae* requires different treatment than infections with other Neisseria species. Infections with nonpathogenic Neisseria such as *N. flava*, *N. sicca*, or *N. subflava* usually require no treatment, whereas infection with pathogens such as *N. meningitidis* may require different antibiotic therapy than *N. gonorrhoeae*.

The identification of *Neisseria gonorrhoeae, Neisseria meningitidis*, and other Neisseria species in the clinical laboratory is usually accomplished by culture and the performance of carbohydrate metabolism tests. Isolates from the cervix, urethra, and rectum are generally not confirmed by a sugar utilization test because other Neisseria species are not generally found at these sites, but isolates from the throat and eye must be confirmed due to nongonococcal strains that give positive presumptive tests for the gonococcus. Confirmation by sugar utilization can be a slow, cumbersome procedure, since a pure culture is required, which can involve several subcultures; even then, results take from 4 hours to 2 days.

Agglutination and coagglutination assays have been developed which use either antibodies or specific lectins as a binder to sites of the gonococcus and are extremely rapid, usually less than fifteen minutes. These tests have limitations because a number of Neisseria strains other than the gonococcus are reactive with lectins, and quite often antibodies are reactive only if the organisms are boiled before being reacted. Monoclonal antibodies have been produced which are specific to the Protein I (principle outer membrane protein) of *Neisseria gonorrhoeae*, but because some of these monoclonals react with only specific serotypes, it is necessary to use a pool of these monoclonal antibodies to recognize all the serotypes.

Horrisberger et al in 1977 in Journal of Histochem & Cytochem 25:295 report the use of colloidal gold labeled antibodies in an immunoassay for mannan. A similar gold sol particle immunoassay, is described by Leuvering in U.S. Pat. No. 4,313,734 (1982). Colloidal gold labeled antibodies have been used extensively in histological studies and have been used in a passive agglutination assay format as described by Geoghegan et al in 1980 Journal of Immunological Methods 34:11.

Gefter et al in U.S. Pat. No. 4,459,361 (1984) discloses a ligand assay with one or two particulate reagents and filter, wherein agglutinated antibody coated dyed particles are separated from nonagglutinated particles by use of a controlled pore size membrane filter. Gould et al in U.S. Pat. No. 4,552,839 (1985) discloses using dyed particles ranging in size from 50 nm to 100 microns which are antibody coated and after reacting with a respective antigen the reactants are allowed to diffuse on a bibulous support where the agglutinated particles will become immobilized when they have reached a certain size and charge.

SUMMARY OF THE INVENTION

The object of the present invention was to overcome shortcomings of nonspecificity and boiling steps of agglutination methods available for the identification and confirmation for *Neisseria gonorrhoeae*. It was a further object of the present invention to provide a simple, rapid, easy to read, noninstrumented method that can be performed in the physicians office or in the clinical laboratory.

The present invention is an immunoassay wherein suspected microorganisms or more specifically *N. gonorrhoeae*, are treated with a detergent solution to expose additional reactive epitopes of the antigen in addition to forming an antigen detergent complex. The detergent treated organisms are reacted with specific colloidal gold labeled antibodies directed against specific antigens of the suspected organism being identified. The mixture is then placed into a device having a small orifice which exposes a surface area no greater than 30 $mm^2$ of a porous support through which the fluid phase of the mixture is permitted to flow. The immunocomplexed gold labeled antibody is captured and concentrated on the surface of the said porous support and the appearance of color in the zone of the small orifice is indicative of the presence of the suspect microorganism.

DESCRIPTION OF THE SPECIFIC EMBODIMENTS

The subject invention is based on the ability of specific porous or fibrous surfaces to immobilize antibody labeled colloidal gold bound to detergent solubilized antigen. The size of the immune complex or immunoprecipitate formed are not a major factor in the immobilization process of the said porous surface as evidenced by the fact that many porous supports with smaller effective pore sizes do not retain adequate quantities of the bound antibody labeled gold reagent. The choice of buffer conditions and detergent will significantly effect the process, indicative that the immobilization is due more to a change in charge as a result of binding to the detergent solubilized membrane fragments.

Amphoteric (zwitterionic) and nonionic detergents in concentrations ranging from 0.001% to 5% have been found to be useful but particularly detergent concentrations of 0.05 to 1.0% have been found to perform optimally in extracting membrane antigens and exhibiting minimal interference of the progression of the antibody antigen reaction. The choice of detergent is not limited to amphoteric and nonionic detergents and those skilled in the art know that different microorganisms may require the use of ionic detergents or a combination of different types of detergents.

The pH conditions and ionic strength of the buffers in the reagents are of importance in influencing the action of the detergents on the microbial antigens and in progression of the immune reaction and therefore will affect the sensitivity of the assay. The pH range of the reactants in the final mixture should be between 5.0 and 10.0, but more particularly between 6.0 and 9.0. The ionic strength of the final reaction mixture should be between 0.01M to 0.50M.

The choice of porous material is of extreme importance to the success of the assay. Glass fiber filters have been found to be extremely specific in immobilizing the labeled complex and because of such specific reactivity does not require any additional washing steps. Cellulose filters, nylon membranes, cellulose acetate, nitrocellulose membranes of pore sizes ranging from 0.2 microns to 5.0 microns have been found to be less effective in the specific immobilization of the complex. The present invention is not-limited to the choice of glass fiber filters because of the knowledge that other filters having similar properties will be satisfactory in the assay.

A feature of the assay is the size of the orifice and the exposed surface area of the porous support. The size of the orifice will allow the colloidal gold labeled antibody to concentrate into a small site, where the naked eye can detect a signal easily. The larger the site, the weaker the signal appears. The size of the exposed surface area of the porous support should be between 0.2 to 30.0 mm$^2$, usually from 8 to 5.0 mm$^2$.

Dyes, pigments, or metal sols such as colloidal gold can be used as a label in the assay provided that the characteristics of the label do not result in nonspecific binding to the porous support and the immobilization of the bound label is visible to the naked eye. Usually the label is colloidal gold of a mean diameter particle size of 10 to 30 nm.

The labeled immunoreactive component of the assay can be any immunological protein, usually monoclonal antibody specific to the suspected organism.

EXAMPLE I

Preparation of colloidal gold labeled monoclonal antibodies to *Neisseria gonorrhoeae*.

Hybrid cell producing monoclonal antibodies directed against the principal outer membrane protein of *N. gonorrhoeae* were produced according to methods described by Tam et al in Infection and Immunity (1982) 36:1042.

Monoclonal antibodies were screened in an ELISA test and selected for reactivity against different gonococcal and nongonococcal strains. The antibodies were purified on a staphyl ococcal protein A sepharose adsorbant column. Each mouse monoclonal was labeled with colloidal gold after determining the minimal amount of protective protein and optimal pH conditions for binding each antibody. Colloidal gold (Janssen pharmaceutical ) 20 nm mean particle size diameter having an optical density at 520 nm of 1.2 was reacted with 6 to 10 micrograms of monoclonal antibody to each milliliter of colloidal gold reagent at a pH ranging from 7.0 to 9.5 depending upon the isoelectric point of each antibody. After reacting the antibody and colloidal gold for two minutes, bovine serum albumen (BSA) was added to a final concentration of 1% and then the mixture was centrifuged at 10000 g for 50 minutes. The pellet was resuspended in 0.02M tris pH 8.2 containing 1% BSA and recentrifuged and resuspended in 0.02M tris pH 8.2 containing 1% BSA and 0.05% sodium azide to a final optical density at 520 nm of 0.6.

The colloidal gold labeled antibodies were tested individually for reactivity against different serotypes of *N. gonorrhoeae* by the present invention. Plastic devices having a funnel shape terminating into a 2 mm diameter orifice in close contact to a 1.2 micron porous glass fiber filter membrane sheet (Whatman) were prepared and placed on an absorbant filter paper.

EXAMPLE II

Performance of an identification and confirmation assay for *N. gonorrhoeae*

A loopful of organisms is suspended to a McFarland 3 standard turbidity in 500 microliters of 0.02M phosphate buffered saline pH 7.2 containing 0.05% zwittergent. Fifty microliters of colloidal gold labeled antibodies are added to the detergent treated organisms and then the mixture is placed on the plastic device wherein the labeled antibody detergent antigen complex is immobilized on the surface of the glass fiber filter. The presence of a red color on the exposed surface of the glass fiber filter indicates the presence of *N. gonorrhoeae, N. gonorrhoeae* organisms at a concentration of 10$^6$ CFU per milliliter can easily be detected.

The results of testing various strains of organisms are summarized in the following table:

| BACTERIAL STRAIN | REACTIVITY* |
|---|---|
| Neisseria strains | |
| 43 nongonococcal | all negative |
| 10 gonococcal (serotypes 1,2,3,4,5,6,7,8,9a,9b) | all positive |
| Non Neisseria strains | |
| L. casei | negative |
| P. mirabilis | " |
| K. oxytoca | " |
| C. freundii | " |
| E. coli | " |
| P. aeruginosa | " |
| Flavobacterium. spp | " |
| S. faecalis | " |
| Alkaligenes. spp | " |
| Moraxella. spp | " |
| K. denitrificans | " |
| K. kingelli | " |

EXAMPLE III

Sensitivity in detecting *N. gonorrhoeae* on seeded swabs

Dacron swabs were seeded with ten microliters of different concentrations of *N. gonorrhoea, N. lactamica* and *N. meningitidis* in order to evaluate the sensitivity and specificity of the test system. The swabs were placed in 180 microliters of 0.02M phosphate buffered saline pH 8.8 containing 10% methanol, 0.05% zwittergent and 0.05% sodium azide extraction buffer to solubilize the principal outer membrane protein of *N. gonorrhoeae*. The extract was reacted with 20 microliters of the gold labeled reagent. After incubating for 2 minutes, the reactants were placed on a 1.2 micron porous glass fiber filter membrane sheet covered with plastic having a 1.5 mm diameter circular orifice. After the liquid phase absorbed by diffusion through the membrane, the color of the orifice was visualized by the naked eye. The results are summarized in the following table:

| CFU | Reactivity* | | |
|---|---|---|---|
| | N. gonorrhoeae | N. lactamica | N. Meningitis |
| $10^8$ | ++++ | +/− | +/− |
| $10^7$ | ++++ | − | − |
| $10^6$ | +++ | − | − |
| $10^5$ | ++ | − | − |
| $10^4$ | ++ | − | − |
| $10^3$ | +/− | − | − |
| $10^2$ | − | − | − |

*+ = intensity of color

The present invention may be embodied in other specific forms without departing from the spirit or essential attributes thereof and, accordingly, reference should be made to the appended claims, rather than to the foregoing specification, as indicating the scope of the invention.

What is claimed is:

1. A method for detecting the presence of a target antigen in a biological specimen, comprising the steps of:
   (a) extracting the antigen from the specimen by contacting the specimen with a first solution comprising a nonionic or zwitterionic detergent to extract the antigen and expose a reactive epitope of the antigen, thereby yielding a second solution;
   (b) contacting the second solution with a colloidal gold-labelled antibody that specifically binds to the antigen to form a colloidal gold-labelled antibody-antigen complex in the solution;
   (c) adding the solution containing the complex to a porous glass fiber filter membrane thereby immobilizing the complex on the membrane, wherein the pore size of the membrane is larger than the size of the complex; and
   (d) visually detecting the presence of the complex on the membrane as an indication of the presence of the antigen in the specimen.

2. The method of claim 1, wherein said biological specimen comprises a microbiological organism.

3. The method of claim 2, wherein said target antigen is extracted from *Neisseria gonorrhoea*.

4. The method of claim 1, wherein the exposed surface area of said porous glass fiber filter membrane is less than 30 mm$^2$.

5. The method of claim 1, wherein said colloidal gold-labelled antibody comprises a colloidal gold particle and at least one antibody.

6. The method of claim 5, wherein said colloidal gold particle has a mean diameter size of less than 50 nm.

7. The method of claim 5, wherein said antibody of said colloidal gold-labelled antibody comprises at least one monoclonal antibody.

8. The method of claim 5, wherein said antibody of said colloidal gold-labelled antibody comprises at least one polyclonal antibody.

9. The method of claim 7, wherein said antigen is extracted from *Neisseria gonorrhoea*.

10. The method of claim 8, wherein said antigen is extracted from *Neisseria gonorrhoea*.

11. The method according to claim 1, wherein in step (d), visually detecting is performed with the naked eye, without the need to add reagents to visualize the presence of said complex.

12. A kit for detecting the presence of a target antigen in a biological specimen, comprising:
   a glass fiber filter membrane, a colloidal gold-labelled antibody which specifically binds to the antigen, and a buffered solution containing a detergent selected from the group consisting of a nonionic detergent and a zwitterionic detergent.

13. A kit according to claim 12, wherein said glass fiber filter membrane has an exposed surface area of less than 30 mm$^2$.

14. A kit according to claim 12, wherein said colloidal gold-labelled antibody comprises a colloidal gold particle and at least one antibody.

15. A kit according to claim 14, wherein the antibody of said colloidal gold-labelled antibody is a monoclonal antibody.

16. A kit according to claim 14, wherein the antibody of said colloidal gold-labelled antibody is a polyclonal antibody.

17. A kit according to claim 14, wherein said particle has a mean diameter size of less than 50 nm.

18. A kit according to claim 15, wherein said antibody is specific for *Neisseria gonorrhoea*.

19. A kit according to claim 16, wherein said antibody is specific for *Neisseria gonorrhoea*.

* * * * *